United States Patent
Barychev et al.

(10) Patent No.: US 9,244,004 B2
(45) Date of Patent: Jan. 26, 2016

(54) METHOD AND SYSTEM FOR INSPECTION OF COMPOSITE ASSEMBLIES USING TERAHERTZ RADIATION

(71) Applicant: Stichting SRON—Netherlands Institute for Space Research, Utrecht (NL)

(72) Inventors: Andrei M. Barychev, Groningen (NL); Alena V. Belitskaya, The Hague (NL); Herman H. Van der Linden, Nuenen (NL); Willem Jellema, Winsum (NL)

(73) Assignee: STICHTING SRON—NETHERLANDS INSTITUTE FOR SPACE RESEARCH, Utrecht (NL)

( * ) Notice: Subject to any disclaimer, the term of this patent is extended or adjusted under 35 U.S.C. 154(b) by 0 days.

(21) Appl. No.: 13/962,210

(22) Filed: Aug. 8, 2013

(65) Prior Publication Data
US 2015/0041654 A1 Feb. 12, 2015

(51) Int. Cl.
*G01N 21/88* (2006.01)
*G01N 21/3581* (2014.01)

(52) U.S. Cl.
CPC .................. *G01N 21/3581* (2013.01)

(58) Field of Classification Search
CPC ............ G01N 21/3581; G01N 21/3586; G01J 2005/0077; G01J 5/02
USPC ...................................... 250/338.4
See application file for complete search history.

(56) References Cited

U.S. PATENT DOCUMENTS

| | | | | |
|---|---|---|---|---|
| 7,378,658 | B2 * | 5/2008 | Mueller et al. | 250/358.1 |
| 7,876,423 | B1 | 1/2011 | Roth | |
| 2005/0098728 | A1 * | 5/2005 | Alfano et al. | 250/341.8 |
| 2007/0090294 | A1 | 4/2007 | Safai et al. | |
| 2007/0257194 | A1 | 11/2007 | Mueller | |
| 2009/0303574 | A1 * | 12/2009 | Gunter et al. | 359/328 |
| 2009/0314944 | A1 | 12/2009 | Evans et al. | |
| 2012/0037804 | A1 * | 2/2012 | Federici | 250/341.1 |

(Continued)

OTHER PUBLICATIONS

Baryshev, et al., "Reflection measurement of absorption coatings using 600-670 GHz vector network analyzer", 18th International Symposium Space Terahertz Technology, Mar. 2007, California Institute of Technology, pp. 157-159.
Durrschmidt et al., "Terahertz Testing of Adhesive Bonds", IEEE, 2011, 2 pages.

(Continued)

*Primary Examiner* — Marcus Taningco
(74) *Attorney, Agent, or Firm* — Edell, Shapiro & Finnan, LLC

(57) ABSTRACT

The present invention relates to a method for non-destructive, contact or non-contact inspection of composite assemblies using radiation having a frequency in the terahertz range (10 GHz-10 THz) of the spectrum, whereby said method is implemented as an embodiment of the system for non-destructive, contact or non-contact inspection of composite assemblies using terahertz radiation, that is also claimed under the present invention. Said method enables the forming of a two or three-dimensional image of the material structure of an assembly of composite materials, from which image detection and analysis of material conditions of the composite materials forming said composite assemblies is possible, irrespective of the way that the composite materials forming said composite assemblies were joined together, and without the need for a priori knowledge about the structural characteristics, shape or configuration of said composite materials (for instance layered, foam, placed on metal substrate).

14 Claims, 1 Drawing Sheet

(56) References Cited

U.S. PATENT DOCUMENTS

2013/0309302 A1* 11/2013 Funke et al. .................. 424/475
2014/0306114 A1* 10/2014 Steckenrider ............ 250/339.11

OTHER PUBLICATIONS

Jansen et al., "Terahertz spectroscopy on adhesive bonds", Polymer Testing 30, 2011, pp. 150-154.

* cited by examiner

METHOD AND SYSTEM FOR INSPECTION OF COMPOSITE ASSEMBLIES USING TERAHERTZ RADIATION

FIELD OF THE INVENTION

The present invention generally relates to a method and system for non-destructive, contact or non-contact inspection of composite assemblies using radiation having a frequency in the so-called "terahertz range" (10 GHz-10 THz) to enable the forming of a two or three dimensional image of the material structure of a said assembly of composite materials, from which image detection and analysis of material conditions of the composite materials forming said composite assemblies is possible, irrespective of the way that the composite materials forming said composite assemblies were joined together, and without the need for a priori knowledge about the structural characteristics, like the shape, or configuration of said composite materials (for instance layered, foam, placed on metal substrate etc.)

BACKGROUND

Nowadays the term "composite materials" or "composites" is often heard when referring to fibre-reinforced polymer materials. Originally, however, the term refers to materials made from two or more constituent materials with significantly different chemical or physical properties, that, when combined, produce a material with different characteristics from the individual components. Although there are also metal composites, the term "composite materials" will hereafter in this document mainly refer to materials that are (partially) transparent for "terahertz radiation". These materials include glass fibre and ceramic materials, as well as different kinds of materials with internal "honeycomb structure" and foams, which are widely used nowadays in especially the aerospace, automotive, nautical and wind energy industries, as well as in building construction and for the production of electronic components. The use of these materials is ever increasing because of their advantageous characteristics like low weight, high strength and high durability. Many essential parts of airplanes, cars, ships, spacecraft and wind turbines are presently made of (assemblies of) composite materials. Safety regulations require that such assemblies of composite materials are regularly inspected for timely detection of possible internal or external structural flaws. Conformity testing even requires that every product undergoes such inspection when it leaves the production line. In most cases it is undesirable to temporarily remove a composite assembly from the structure of which it forms a part, for inspection, for instance because of the operation schedule of an aircraft, or because of the size of the composite assembly, for instance in case of a ship hull. A solution to this is to bring the inspection equipment to the composite assembly that is to be inspected. This is called "non-destructive testing". In case the inspection method does not require any contact between the inspection system and the composite assembly, this is called "non-contact testing". However, the method according to the present invention is also suited for contact testing. In some situations it may be important that changes in material conditions and structural integrity are detected as they occur and can be monitored in real time. This is called "condition monitoring". The method according to the present invention can also be advantageously applied in situations where such condition monitoring is required.

Some of the more traditional non-destructive inspection methods, known from prior art, are the ones using for instance X-rays or ultrasound. The main drawback of the use of X-ray inspection of composite assemblies is the need for additional safety requirements which makes large scale application less feasible commercially. A serious drawback of the use of ultrasound for inspection of composite assemblies is the fact that the ultrasound waves are scattered (no transmission, no reflection), partially or completely, by many of the adhesives that are frequently used in composite assemblies. Because of the mentioned drawbacks, X-ray and ultrasound inspection are not suitable for many applications where inspection of composite assemblies is required.

At the end of the 1990's so-called "terahertz imaging" emerged as a tool for inspection of material structures. The THz frequency range is the frequency range between, approximately, 10 GHz and 10 THz, between the microwave and infrared parts of the spectrum. The use of THz radiation makes excellent contrast mechanisms and high resolution imaging possible. Non-polar liquids, dielectric solids and gases are at least partially transparent for THz radiation, while metallic surfaces totally reflect THz waves. The main fields of application were originally security (detection of the material of, for instance, concealed weapons and explosives) at airports, analysing biological materials, analysing dielectric materials, determining geometrical properties of objects, like length, width and thickness, determining material properties like density and contamination and imaging of objects and material samples (for instance layered structures).

Initially the equipment to be used to produce, detect or process terahertz radiation was very expensive, hence widespread use was not economically feasible and remained limited. Since about 2005 this gradually changed because of new technological developments in the THz field, and an increasing number of THz systems and components have been developed and patented since then.

The object of the present invention is to present a method for non-destructive, contact or non-contact inspection of composite assemblies using terahertz radiation, whereby at least one of the materials in the assembly is (partially) transparent for said terahertz radiation, which method is independent of the way that the composite materials forming said composite assemblies were joined together, and without the need for a priori knowledge about the structure, shape or configuration of said composite materials (for instance layered, foam, placed on metal substrate etc.)

From prior art several methods are known for inspection of material structures using THz radiation. For instance the document US 2007/0090294 A1 describes a method where a liquid is applied to the surface of an object under test, whereby the said liquid absorbs THz radiation in a different manner than the structure/material of the object under test and thus provides the contrast for THz imaging. A significant drawback of the said method is the fact that it is limited to inspection and detection of surface material conditions, like cracks and recesses, that are in direct contact with the object surface so that the said liquid can penetrate. Another serious drawback is the fact that the method requires that excess liquid is removed from the object before imaging. This requires cumbersome actions like wiping, heating or blow-drying. The method according to the present invention is not limited to surface inspection and requires no additional actions like the use of fluids for imaging contrast purposes.

Another prior art document, U.S. Pat. No. 7,876,423 B1, is directed at detecting microstructural and thickness variations in dielectric materials using THz energy. The described method is mainly directed to the inspection of sprayed-on foam on a metal container, i.e. the Space Shuttle external fuel tank thermal protection and is not specifically directed at the inspection of composite assemblies. The method according to the present invention does not require prior knowledge about the structure, shape and configuration of the materials under inspection. It suffices to know that at least one of the materials in the assembly under inspection is (partially) transparent for terahertz radiation.

The non-patent prior art references C. Jansen, S. Wietzke, H. Wang, M. Koch and G. Zhao, "Terahertz Spectroscopy on Adhesive Bonds", Polymer Testing, 2011, 30(1), pp. 150-154, and S. F. Durrschmidt, S. Wietzke, C. Jansen, H. Wang and G. Zhao, "Terahertz testing of adhesive bonds", 36th. International Conference on Infrared, Millimeter and Terahertz waves (IRMMW-THz), 2011, pp. 1-7, are concerned with inspecting the integrity of adhesive bonds between polymer materials. It should be clear to the reader that the method according to the present invention is not limited to the inspection of adhesive bonds but is aimed at the detection and analysis of a wide range of material conditions within composite assemblies (for instance cracks, recesses, internal cavities, damaged adhesive joints, density or thickness variations, porosity, delamination, inclusions, etc.)

As such the method according to the present invention aims to provide solutions for the limitations and drawbacks associated with the prior art in the relevant field.

The present invention further relates to a system for non-destructive, contact or non-contact inspection of composite assemblies using terahertz radiation, said system according to the present invention being characterised in that the system comprises such electronic and electro-optical components that it can illuminate an assembly of composite materials with radiation having a frequency in the so-called "Terahertz range" (10 GHz-10 THz.), detect the radiation reflected from and/or transmitted through the said assembly of composite materials, record the spatially resolved reflection and/or transmission responses, construct a two or three-dimensional image from the said spatially resolved reflection and/or transmission components and present said image to the user of the system. This enables measurement of the amplitude and phase of the detected signal with very high dynamic range (>60-70 dB) and construction of high-detail output images.

The document A. M. Baryshev, W. Jellema, R. Hesper, W. Wild, "Reflection Measurement of Absorption Coatings using 600-670 GHz Vector Network Analyzer", 18th International Symposium on Space Terahertz Technology, March 2007, California Institute of Technology, Pasadena, Calif., USA, discloses the construction and function of a Vector Network Analyzer (VNA) that is equipped with such tunable solid state submm signal sources, that the function of the VNA is extended into the terahertz frequency range. Some of the advantageous characteristics of the said extended VNA, that was developed by SRON—The Netherlands Institute for Space Research, are employed within the system according to the present invention, to enable the forming of a two or three-dimensional image of the material structure of an assembly of composite materials, from which image detection and analysis of material conditions of the composite materials forming said composite assemblies is possible, provided that at least one of the composite materials in the assembly is (partially) transparent for said terahertz radiation, but irrespective of the way that the composite materials forming said composite assemblies were joined together, and without the need for prior knowledge about the structure, shape or configuration of said composite materials (for instance layered, foam, placed on metal substrate etc.). As such the method according to the present invention aims to provide solutions for the limitations and drawbacks associated with the prior art in the relevant field.

SUMMARY OF THE INVENTION

From the description as given hereinafter, the advantageous characteristics of the method and system of the present invention will become clear to the reader. The reader should however note that the characteristics and embodiments that are described, are merely meant to illustrate the advantageous features of the method and system of the present invention and are in no way whatsoever meant to limit its application possibilities.

In an advantageous embodiment the method, according to the present invention, for non-destructive, contact or non-contact inspection of composite assemblies using radiation having a frequency in the so-called "terahertz range" (10 GHz-10 THz) of the spectrum, whereby said method is implemented as an embodiment of the system for non-destructive, contact or non-contact inspection of composite assemblies using terahertz radiation that is also claimed under the present invention, is characterised in that the method enables the forming of a two or three dimensional image of the material structure of a said assembly of composite materials, from which detection and analysis of material conditions of the composite materials forming said composite assemblies is possible, irrespective of the way that the composite materials forming said composite assemblies were joined together, provided that at least one of the composite materials in the assembly is (partially) transparent for said terahertz radiation, but without the need for a priori knowledge about the structure, shape or configuration of said composite materials. A particular advantage over prior art is the fact that the method of the present invention is not limited to the detection and analysis of specific material conditions, but can be used for a wide range of material conditions, like for instance cracks, recesses, internal cavities, damaged adhesive joints, density or thickness variations, etc. This enables a wide range of applications.

The method according to the present invention for non-destructive, contact or non-contact inspection of composite assemblies using terahertz radiation, is furthermore advantageously characterised by the fact that said method at least comprises the following steps:
  illuminating a composite assembly that is to be inspected with radiation from the so-called terahertz frequency range from the spectrum, being the range 10 GHz to 10 THz between microwave and infrared;
  detect the radiation reflected by and/or transmitted through the said composite assembly and record the spatially resolved reflection and/or transmission responses;
  automated construction of a two or three-dimensional THz image from the said spatially resolved reflection and/or transmission responses, presenting said image in a way that enables detection and analysis of specific material conditions (for instance cracks, recesses, internal cavities, damaged adhesive joints, density or thickness variations) of the composite materials forming the assembly.

With the use of THz radiation, the reflection and/or transmission responses enable measurement of the signal phase and amplitude as a function of frequency with very high dynamic range (>60-70 dB), which significantly improves measurement accuracy, and consequently resolution and contrast of the output image.

In a preferred embodiment, the system for non-destructive, contact or non-contact inspection of composite assemblies using terahertz radiation, is advantageously characterised in that the system comprises such electronic and electro-optic components that it can illuminate an assembly of composite materials with radiation having a frequency in the so-called "Terahertz range" (10 GHz-10 THz.), detect the radiation reflected by and/or transmitted through the said assembly of composite materials, record the spatially resolved reflection and/or transmission responses, construct a two or three-dimensional image from the said spatially resolved reflection and/or transmission components and present said image to the user of the system.

Depending on the literature source, the definition of "Terahertz range" may slightly differ. The said construction of the said image and the said presentation of the image are achieved by commonly known software algorithms and (computer) hardware.

In yet another advantageous embodiment, the system for non-destructive, contact or non-contact inspection of composite assemblies using terahertz radiation according to the present invention is characterised in that the system comprises a Vector Network Analyzer (VNA) with at least one radiation source and at least one radiation detector that are able to produce/detect radiation with frequencies in the terahertz range.

A standard VNA measures phase and amplitude of the reflected and/or transmitted radiation signal. Normally a VNA needs at least two receivers (detectors) to accurately measure the phase of the reflected and/or transmitted radiation signal, using a reference signal. Recent developments in electronically tuneable submm solid state devices technology has enabled to extend the function of the VNA into the terahertz range.

In a further advantageous embodiment of the system for non-destructive, contact or non-contact inspection of composite assemblies using terahertz radiation according to the present invention, the system for non-destructive, contact or non-contact inspection of composite assemblies using terahertz radiation uses a subharmonically pumped superlattice device as receiver/detector for reflected and/or transmitted terahertz radiation.

These devices are in fact planar diodes based on a semiconductor quantum superlattice, which can be advantageously applied in the terahertz frequency range.

In yet another embodiment of the system for non-destructive, contact or non-contact inspection of composite assemblies using terahertz radiation according to the present invention the said radiation detector is a Schottky diode or an amplifier followed by a Schottky diode.

The use of Schottky diodes is in fact a more classical approach towards the realisation of radiation detectors. Nowadays however their use has been extended to the terahertz frequency range, because present semiconductor Schottky diodes can be advantageously used as direct detectors throughout the Millimeter and subMillimeter wavelength bands. When optimised to have a low forward turn-on voltage, the diodes can achieve excellent frequency response and bandwidth.

In a further preferred embodiment of the system for non-destructive, contact or non-contact inspection of composite assemblies using terahertz radiation according to the present invention, the said single port quasi-optical Vector Network Analyzer is configured as a Michelson reflectometer which at least comprises:
- a terahertz radiation source;
- a terahertz radiation detector;
- a beam splitter in the form of a "half-silvered" mirror with a Mylar, Kapton or Surlyn (All® DuPont), Aclar (® Honeywell), silicon, CVD diamond or other suitable dielectric thin film material to transmit the source radiation towards the composite assembly under inspection, and to deflect the radiation reflected and/or transmitted by said composite assembly under 90 degrees towards the radiation detector;
- 2 High-density poly-ethylene (HDP) lenses in the radiation path in front of the terahertz source and the terahertz detector;
- a beam dump load to cancel out parasitic radiation components.

The Michelson quasi-optical reflectometer configuration was advantageously selected to convert the said VNA into a single port reflectometer that can function in the terahertz frequency region.

In another preferred embodiment of the system for non-destructive, contact or non-contact inspection of composite assemblies using terahertz radiation, the system comprises multiple terahertz radiation detectors that are arranged in a detector array.

The use of multiple detectors enables better stability, better phase calibration and even polarimetric measurements.

In yet another preferred embodiment of the system for non-destructive, contact or non-contact inspection of composite assemblies using terahertz radiation, at least the said terahertz radiation source and the said terahertz radiation detector or the said terahertz radiation detector array, are combined in a scanning device, that at least enables to position the terahertz source radiation on different areas or locations on the outer surface of the composite assembly under investigation, or to direct said source radiation in the form of a scanning beam towards different areas or locations on the outer surface of the composite assembly under investigation, and to illuminate said outer surface of said composite assembly according to predefined scanning patterns.

This enables repeated investigation for specific composite assemblies under investigation or for series of similar composite assemblies, by storing the specific scanning patterns and corresponding results to enable detection of changes in the material structure.

In an advantageous embodiment, the system for non-destructive, contact or non-contact inspection of composite assemblies using terahertz radiation all of the mentioned components are integrated in one device in the form of semiconductor electronic and electro-optical components, integrated waveguides etc.

Such integration enables a high mobility of the resulting device implementing the system according to the present invention, which may even be hand-held, thus significantly increasing the range of application of the said system.

In a system for non-destructive, contact or non-contact inspection of composite assemblies using terahertz radiation according to the present invention, the said construction of the said two or three-dimensional image from the said spatially resolved reflection and/or transmission components, and the presentation of the resulting image to a user are achieved by commonly available (computer) hardware and commonly known software algorithms.

In an advantageous embodiment of the system according to the present invention, the said (computer) hardware and software algorithms for construction and presentation of the resulting THz images to a user are integrated into the VNA device. The resulting image data may however also be entered into an external (computer) system for presentation and analysis purposes.

DETAILED DESCRIPTION

In the following a preferred embodiment of the system according to the present invention will be described with reference to the attached drawings. The following description of said preferred embodiment will show to the reader in more detail how the invention remedies the aforementioned disadvantages associated with the prior art. However, the reader should observe that the description and the drawings are merely meant to illustrate application of the invention and should in no way be regarded as limiting the scope of the present invention.

Figure 1:
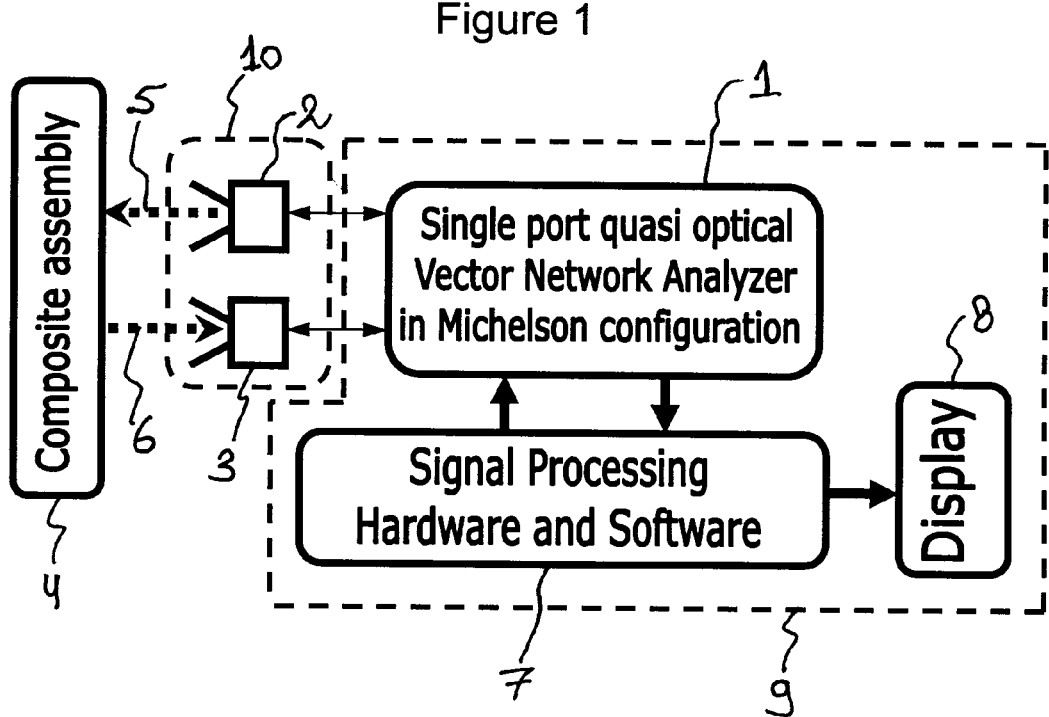
FIG. 1 is a schematic diagram of a preferred embodiment of the system according to the present invention.

FIG. 1 shows a composite assembly (4) that is to be inspected to detect material conditions like for instance cracks, recesses, internal cavities, damaged adhesive joints, density, thickness variations, porosity, delamination or inclusions). For this purpose the system according to the present invention employs a Single Port quasi-optical Vector Network Analyzer (VNA) in Michelson configuration (1) as was designed at SRON—The Netherlands Institute for Space Research. The VNA (1) comprises a radiation source (2) that enables the illumination of the composite assembly (4) with radiation (5) having a frequency in the terahertz range 420-1980 GHz. To detect the radiation (6) reflected by the composite assembly (4), the VNA (1) comprises a detector (3). In this embodiment of the system according to the present invention, the detector (3) is either a Schottky diode for a frequency range of 420-1100 GHz, or a sub-harmonically pumped superlattice device for a frequency range of 420-1980 GHz. The source and detector are in this particular embodiment detached from the rest of the system into a separate scanning device (10). This scanning device (10) comprises such electro-mechanical means that the source (2) and the detector (3) can be positioned in three dimensions with respect to the composite assembly (4) under investigation, so that the outer surface of said composite assembly can be illuminated with THz radiation on a point-by-point basis, according to pre-defined scanning patterns.

Figure 2:
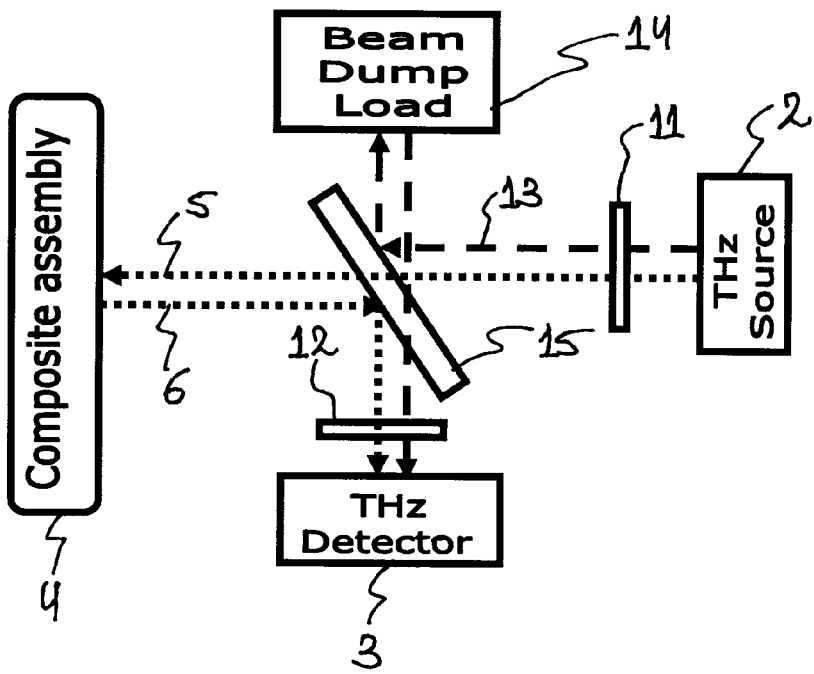
FIG. 2 is a schematic diagram of the single port quasi-optical Vector Network Analyzer in Michelson configuration that forms a part of the said preferred embodiment shown in FIG. 1 of the system according to the present invention.

The said radiation source (2) and detector (3) are also shown in FIG. 2 which gives a more detailed schematic view of the single port quasi-optical Vector Network Analyzer in Michelson configuration (1). In FIG. 2 THz radiation source (2) emits THz radiation (5) and a parasitic signal component (13). Both pass through a HDP (High Density Poly-ethylene) lens (11) and reach beam splitter (15) which is a "half-silvered (one-way) mirror" coated with a 40 micron thin layer of Mylar (® DuPont). The main THz radiation beam (5) passes through said beam splitter (15) and the parasitic component is deflected 90 degrees towards Beam Dump Load (14) where it is absorbed. The main THz beam (5) falls on the composite assembly (4) and the resulting reflection beam (6) is deflected over 90 degrees by beam splitter (15) and arrives through a second HDP lens (12) at THz detector (3). Now the reflection responses are recorded and spatially resolved by signal processing hardware and software (7). The signal information is further processed to construct a two or three-dimensional image of the material structure of the composite assembly which is subsequently presented to the user of the system by means of a display (8). The said image can then be used to inspect and analyse the material structure(s) of the composite assembly (4). The reader shall note that the mentioned signal processing hardware and software (7) is no object of the present invention and comprises commonly known and commonly available technology. Preferably the VNA (1) is integrated together with signal processing hardware (7) and display (8) in a single device (9). This improves the mobility of the system according to the present invention and thus increases the range of application of the said system.

From the foregoing description it may be clear to the reader that the system according to the present invention offers solutions to numerous drawbacks associated with the prior art in this field. In addition to this, all parts of the described preferred embodiment of the system according to the present invention are commonly available or can be manufactured by using commonly available materials and commonly known production methods.

What is claimed is:

1. A method for non-destructive, contact or non-contact inspection of a composite assembly using radiation having a frequency in the so-called "terahertz range" (10 GHz-10 THz) of the spectrum, the composite assembly comprising composite materials joined together, whereby at least one of the composite materials in the assembly is, at least, partially transparent for said terahertz radiation, said method being characterised in that the method enables the forming of a two or three-dimensional image of the material structure of a said assembly of composite materials, from which detection and analysis of material conditions of the composite materials forming said composite assemblies is possible, irrespective of the way that the composite materials forming said composite assemblies were joined together, and without the need for a priori knowledge about the structure, shape or configuration of said composite materials, the method comprising the following steps:
illuminating a composite assembly that is to be inspected with radiation from the so-called terahertz frequency range from the spectrum, being the range 10 GHz to 10 THz between microwave and infrared;
detecting the radiation reflected by and/or transmitted through the said composite assembly and record spatially resolved reflection and/or transmission responses; and
automating construction and presentation of a two or three-dimensional THz image from the said spatially resolved reflection and/or transmission responses, and presenting said image in a way that enables detection and analysis of specific material conditions of the composite materials forming the assembly,
wherein the illuminating and detecting are performed by a single port quasi-optical VNA configured as a Michelson reflectometer.

2. The method according to claim 1, wherein detecting the radiation reflected by and/or transmitted through the said composite assembly and recording the spatially resolved reflection and/or transmission responses comprises:
measurement of signal phase and amplitude as a function of frequency.

3. The method according to claim 1, wherein the specific material conditions of the composite materials forming the assembly comprise at least one of cracks, recesses, internal cavities, damaged adhesive joints, density or thickness variations, porosity, delamination, inclusions.

4. A system configured for non-destructive, contact or non-contact inspection of composite assemblies using terahertz radiation, the composite assembly comprising composite materials joined together, characterised in that the system comprises electronic and electro-optic components and being configured to:
illuminate an assembly of composite materials with radiation having a frequency in the so-called "Terahertz range" (10 GHz-10 THz), detect the radiation reflected by and/or transmitted through the said assembly of composite materials, record spatially resolved reflection and/or transmission responses, construct a two or three-dimensional image from the said spatially resolved reflection and/or transmission components and present said image to the user of the system, the system comprising a single port quasi-optical Vector Network Analyzer (VNA) configured as a Michelson reflectometer.

5. The system of claim 4, for non-destructive, contact or non-contact inspection of composite assemblies using terahertz radiation, wherein the VNA comprises at least one radiation source and at least one radiation detector that are able to produce/detect radiation with frequencies in the terahertz range.

6. The system of claim 5, for non-destructive, contact or non-contact inspection of composite assemblies using terahertz radiation, characterised in that the said radiation detector is a subharmonically pumped superlattice device.

7. The system of claim 5, for non-destructive, contact or non-contact inspection of composite assemblies using terahertz radiation, characterised in that the said radiation detector is a Schottky diode or an amplifier followed by a Schottky diode.

8. The system of claim 5, for non-destructive, contact or non-contact inspection of composite assemblies using terahertz radiation, wherein the VNA comprises:
   a terahertz radiation source;
   a terahertz radiation detector;
   a beam splitter to transmit the source radiation towards the composite assembly under inspection, and to deflect the radiation reflected and/or transmitted by said composite assembly under 90 degrees towards the radiation detector;
   two High-density poly-ethylene (HDP) lenses in the radiation path in front of the terahertz source and the terahertz detector; and
   a beam dump load to cancel out parasitic radiation components.

9. The system of claim 5, for non-destructive, contact or non-contact inspection of composite assemblies using terahertz radiation, characterised in that the system comprises multiple terahertz radiation detectors that are arranged in a detector array.

10. The system of claim 5, for non-destructive, contact or non-contact inspection of composite assemblies using terahertz radiation, characterised in that at least the said terahertz radiation source and the said terahertz radiation detector, or the said terahertz radiation detector array, are combined in a scanning device, that at least enables to position the terahertz source radiation on different areas or locations on the outer surface of the composite assembly under investigation, or to direct said source radiation in the form of a scanning beam towards different areas or locations on the outer surface of the composite assembly under investigation, and to illuminate said outer surface of said composite assembly according to predefined scanning patterns.

11. System for non-destructive, contact or non-contact inspection of composite assemblies using terahertz radiation according to claim 5, characterised in that all of the mentioned components of the said system are integrated in one device in the form of semiconductor electronic and electro-optical components.

12. System for non-destructive, contact or non-contact inspection of composite assemblies using terahertz radiation according to claim 5, characterised in that the said construction of the said two or three-dimensional image from the said spatially resolved reflection and/or transmission components, and the presentation of the resulting image to a user are achieved by commonly available (computer) hardware and commonly known software algorithms.

13. The system according to claim 4, wherein the system being configured to measure signal phase and amplitude as a function of frequency.

14. The system according to claim 4, wherein the specific material conditions of the composite materials forming the assembly comprise at least one of cracks, recesses, internal cavities, damaged adhesive joints, density or thickness variations, porosity, delamination, inclusions.

* * * * *